(12) United States Patent
McGill et al.

(10) Patent No.: US 8,409,510 B2
(45) Date of Patent: Apr. 2, 2013

(54) MICRO SCALE FLOW THROUGH SORBENT PLATE COLLECTION DEVICE

(75) Inventors: Robert Andrew McGill, Lorton, VA (US); Michael Martin, Louisville, KY (US); Mark Crain, Georgetown, IN (US); Kevin Walsh, Louisville, KY (US); Eric Houser, Ocean View, NJ (US); Stanley Vincent Stepnowski, Alexandria, VA (US); Viet Nguyen, Gaithersburg, MD (US)

(73) Assignees: The United States of America as represented by the Secretary of the Navy, Washington, DC (US); University of Louisville Research Foundation, Inc., Louisville, KY (US)

( * ) Notice: Subject to any disclaimer, the term of this patent is extended or adjusted under 35 U.S.C. 154(b) by 1003 days.

(21) Appl. No.: 11/542,453

(22) Filed: Oct. 2, 2006

(65) Prior Publication Data
US 2010/0120167 A1    May 13, 2010

Related U.S. Application Data

(63) Continuation of application No. 10/865,685, filed on Jun. 10, 2004, now abandoned.

(60) Provisional application No. 60/477,032, filed on Jun. 10, 2003.

(51) Int. Cl.
*G01N 30/00* (2006.01)
*G01N 30/08* (2006.01)
*G01N 30/90* (2006.01)

(52) U.S. Cl. ........... 422/88; 422/89; 422/527; 73/23.35; 73/23.41; 96/101; 96/108; 96/112

(58) Field of Classification Search .................... 422/69, 422/70, 89, 101, 88, 527; 436/161, 178; 95/82, 87, 90, 106; 96/101, 104, 108, 112, 96/117.5; 210/660, 662; 73/23.35, 23.41, 73/61.52, 61.55
See application file for complete search history.

(56) References Cited

U.S. PATENT DOCUMENTS

| | | | |
|---|---|---|---|
| 3,768,300 A | 10/1973 | Nemeth |
| 4,935,040 A | 6/1990 | Goedert |
| 5,174,797 A | 12/1992 | Yow, Sr. et al. |
| 5,465,607 A | 11/1995 | Corrigan et al. |
| 5,690,763 A | 11/1997 | Ashmead et al. |
| 5,707,502 A | 1/1998 | McCaffrey et al. |
| 5,720,798 A | 2/1998 | Nickerson et al. |
| 5,817,012 A | 10/1998 | Schoendorfer |
| 5,970,803 A | 10/1999 | Staples et al. |
| 6,171,378 B1 | 1/2001 | Manginell et al. |
| 6,242,195 B1 | 6/2001 | Idusogie et al. |
| 6,442,997 B1 | 9/2002 | Megerle |
| 6,527,835 B1 | 3/2003 | Manginell |
| 6,666,907 B1 | 12/2003 | Manginell |

(Continued)

OTHER PUBLICATIONS

R.A. McGill, M.H. Abraham, J.W. Grate, "Choosing Polymer Coatings for Chemical Sensors", Chemtech, Sep. 1994, pp. 27-37.

(Continued)

*Primary Examiner* — Jan Ludlow
(74) *Attorney, Agent, or Firm* — Wyatt, Tarrant & Combs, LLP; Stephen C. Hall

(57) ABSTRACT

In the invention, a collection device includes a flow through micro scale plate arranged to collect analyte. The plate includes holes, and sorbent coating on contact surfaces of the plate. The holes pass analyte fluid flow, for example analyte vapor so that fluid flow for collection may be generally perpendicular to the sorbent plate. Preferred embodiment plates include an integrated heater trace. In preferred embodiments, a high substantially perpendicular flow is used for collection and concentration, and during desorption and delivery a low substantially parallel flow is used. The low flow is selected to meet constraints of a detector system.

27 Claims, 13 Drawing Sheets

U.S. PATENT DOCUMENTS

| | | |
|---|---|---|
| 6,759,013 B2 | 7/2004 | Kaltenbach et al. |
| 6,893,879 B2 | 5/2005 | Peterson et al. |
| 6,989,891 B2 | 1/2006 | Braig et al. |
| 7,118,712 B1 | 10/2006 | Manginell et al. |
| 7,306,649 B2 | 12/2007 | Boyle et al. |
| 2003/0106799 A1 | 6/2003 | Covington et al. |
| 2005/0226778 A1 | 10/2005 | Houser |
| 2008/0148815 A1 | 6/2008 | Lucas et al. |
| 2009/0028208 A1 | 1/2009 | Martin |

OTHER PUBLICATIONS

Hughes et al., "A MEMS Based Hybrid Preconcentrator/Chemiresistor Chemical Sensor," Sep. 1, 2002.

Micro Analytical Systems Department Technology—ChemLab, Fact Sheet, Sandia Corporation, Dec. 30, 2002.

MICRO SCALE FLOW THROUGH SORBENT PLATE COLLECTION DEVICE

REFERENCE TO RELATED APPLICATIONS AND PRIORITY CLAIM

This application is a continuation of U.S. application Ser. No. 10/865,685, filed Jun. 10, 2004 now abandoned, which claims priority from U.S. provisional application Ser. No. 60/477,032, filed on Jun. 10, 2003.

This application is also related to application Ser. No. 10/868,445, entitled MICRO SCALE FLOW THROUGH SORBENT PLATE COLLECTION DEVICE, filed on Jun. 10, 2004.

STATEMENT OF GOVERNMENT INTEREST

This invention was made with Government assistance under NRL grant No. N00173-02-2-C002. The Government has certain rights in this invention.

FIELD OF THE INVENTION

A field of the invention is analyte collection. The invention is useful, for example, in analyte detection and analysis systems and methods, as might be used for the collection, detection and analysis of a wide range of vapors or gases, particulate and liquid bound analytes. Another field of the invention is analyte storage and delivery. The invention is useful, for example, to store and deliver hazardous materials, including explosive related materials, toxic industrial chemicals (TICS), or chemical or biological agents or toxins in a controlled manner.

BACKGROUND OF THE INVENTION

In many analytical systems, discovering the nature of an unknown substance normally requires the substance to first be collected. There are detector systems that analyze a fluid flow analyte stream, i.e., vapors or gases, particulates and liquid bound analytes. Some detector systems are based, for example, on an optical analysis that determines analyte characteristics by subjecting a quantity of the analyte to a light beam and measuring the scattering or fluorescence effects. Chromatography detector systems, for example, are sometimes based upon the optical effects produced by analyte samples. There are both quantitative and qualitative analysis detector systems.

Before a sample may be analyzed by chromatography or by many other types of analytical techniques, the sample must be collected and then delivered to a chromatographic column or a detector system. Many samples of interest are available outside of a controlled setting. One important use for analyte analysis is for safety testing of environments that humans occupy. There is a heightened awareness in modern times of the potential for the intentional detonation of explosives or release of chemical or biological agents into environments occupied by humans. The environments might include open or enclosed spaces in work environments, public environments, or military environments, etc. Many building environments with ducted HVAC (heating ventilation and air conditioning) have the potential for the intentional release of TICS or chemical and biological agents into closed or open spaces occupied by military or civilian personnel. Manufacturing operations also have the potential to permit the escape of hazardous chemicals or biological agents into a manufacturing environment or to an external environment surrounding a manufacturing plant.

In some situations, detection may be desirable in a matter of seconds, but in others, an extended period of time may be used for collection before performing an analysis. An example of the latter case involves workers that may be exposed over a time period to unacceptable levels of harmful agents. Another example of the latter case is when cargo containers are transported from country to country by sea, it may be desirable to collect a sample over a period of several days prior to analysis.

In both uncontrolled settings and controlled settings, analytical resolution and the sensitivity of detection are dependent upon the efficiency of analyte collection and the efficacy of delivery of collected analyte to a detection system. It is desirable, for example, to detect very low levels of toxic or hazardous materials in a particular environment. Gas chromatography and other analytical techniques can employ a variety of detector types, and they have been demonstrated to be very sensitive types of analysis techniques, for example. Another example is a chemresistor based device, which uses a detector whose resistivity changes when it is exposed to particular chemical vapors. Whatever the type of detector system, however, concentrating analyte in a stage prior to the detector system can improve detection limits for the analyte(s) of interest, and can also provide a more reliable quantitative or qualitative determination of an analyte.

Constructing a portable field instrument for collection, storage, concentration, and possibly on-site analyte analysis also presents challenges. Compactness is an important factor to provide an instrument that is useful in the field, but one that competes with other design constraints in the case of a portable field instrument. Among other important factors are the sensitivity discussed above, the time scale required to collect and analyze a sample (preferably short), the amount of fluid flow that may be achieved (limited by tolerable pressure drops and pump capacity) while maintaining good analyte-sorbent material interaction, and the amenability of a device's collection hardware to be integrated with other parts of a field instrument. Low weight, durability, and low electrical power consumption are also desirable qualities for prolonged field use.

A known analyte collection and detector system arrangement uses a direct pneumatic sampling. A direct pneumatic sampling makes only a small portion of available analyte available to the detector system in any given time period. One technique of compensating for the low levels of analyte provided to the detector system involves taking a detector system signal over an extended time period. A typical strategy is to deliver a continuous or broad time pulse of analyte vapor to the detector system, e.g., a pulse extended from a few seconds to tens of seconds. This is employed with a detector system having relatively fast signal kinetics. An analyte signal is produced over an extended period of time, e.g., a broad flat curve lacking a sharp signal that may have a low and somewhat indistinct maximum value that is vulnerable to baseline shifts. The maximum signal value is dependent on the analyte concentration, the detector system characteristics and the time width of the vapor pulse sampled.

Others have worked on concentrating analytes, and have proposed systems including a micro scale collection section. A group working at Sandia National Laboratory in Albuquerque, N. Mex. has developed chemical preconcentrators including a preconcentrator heated plate that incorporates a sorbent material coating. This work is discussed, for example, in Manginell et al. U.S. Pat. No. 6,257,835, entitled Chemical Preconcentrator with Integral Thermal Flow Sensor and in Manginell et al. U.S. Pat. No. 6,171,378, entitled Chemical Preconcentrator. The chemical preconcentrator used in that work is formed from a substrate having a suspended membrane, such as low-stress silicon nitride. A resistive heating element is deposited over the membrane and coated with a sorbent, such as a hydrophobic sol-gel coating or a polymer coating. A fluid flow is passed over the sorbent to achieve a collection. A high concentration may then be delivered to a detector system by desorbing, which is achieved by heating the resistive heating element.

One advantage of this work by Manginell and others is that it can provide a relatively high concentration of analyte by collecting it over a long period, and then delivering it in a short amount of time. Another advantage is the MEMS (microelectromechanical systems) micro scale of the device and the MEMS fabrication techniques that permit integration of the device with other system components, for example to form a micro analytical system.

In another style of analyte collector, a column that is packed with a porous adsorbent is used to collect analyte by flowing air through the column and thermally desorbing collected material. The pressure drop associated with this sort of device is typically too high for high flow applications and requires higher power consumption. If the amount of adsorbent is minimized to allow higher flows or faster desorption, the dynamic range is compromised.

However, the inventors have recognized drawbacks in the known prior devices. With embodiments of the present invention, some or all of these drawbacks are overcome. One limitation of known prior devices is the reliance upon a flow arrangement where fluid flow during collection is generally passed over the sorbent in a direction generally parallel to its surface. Taking the example of an analyte vapor being passed over the sorbent coated preconcentrator of the Sandia work, much of the analyte vapor avoids contacting the sorbent in its flow over design. Increasing contact between the analyte fluid flow and the sorbent in the collection area would require creating a turbulent flow, a difficult task given the practical requirements including, for example, constraints such as a limitation on the amount of pressure drop. Flow could be increased, as well, but designs have generally looked away from high flow rates because the designs gravitate toward the generally low flow rates that provide optimal operating conditions for detector systems, such as gas column chromatography detector systems. In addition, if the dimensions of the pneumatic pathway that encloses the preconcentrator in the Sandia work were widened to afford a lower pressure drop across the device, and afford a higher flow rate capability, then the percentage of analyte vapor interacting with the sorbent would dramatically decrease. Artisans have typically viewed the flow rate of the detector system as a necessary limitation on a collection system, whereas embodiments of the invention permit collection flow rates well in excess of the flow rate that is well-tolerated by a detector system intended to be used in conjunction with preferred embodiment collection devices.

SUMMARY OF THE INVENTION

In the invention, a collection device includes a flow through micro scale plate arranged to collect analyte. The plate includes penetrating holes, and sorbent coating on contact surfaces of the plate. The holes pass analyte fluid flow, for example analyte vapor, so that fluid flow for collection may be generally perpendicular to the sorbent plate. Preferred embodiment plates include an integrated heater trace. In preferred embodiments, a high substantially perpendicular flow is used for collection and concentration, and during desorption a low substantially parallel flow is used. The low flow is selected to match constraints of a detector system.

DETAILED DESCRIPTION OF THE PREFERRED EMBODIMENTS

Figure 1:
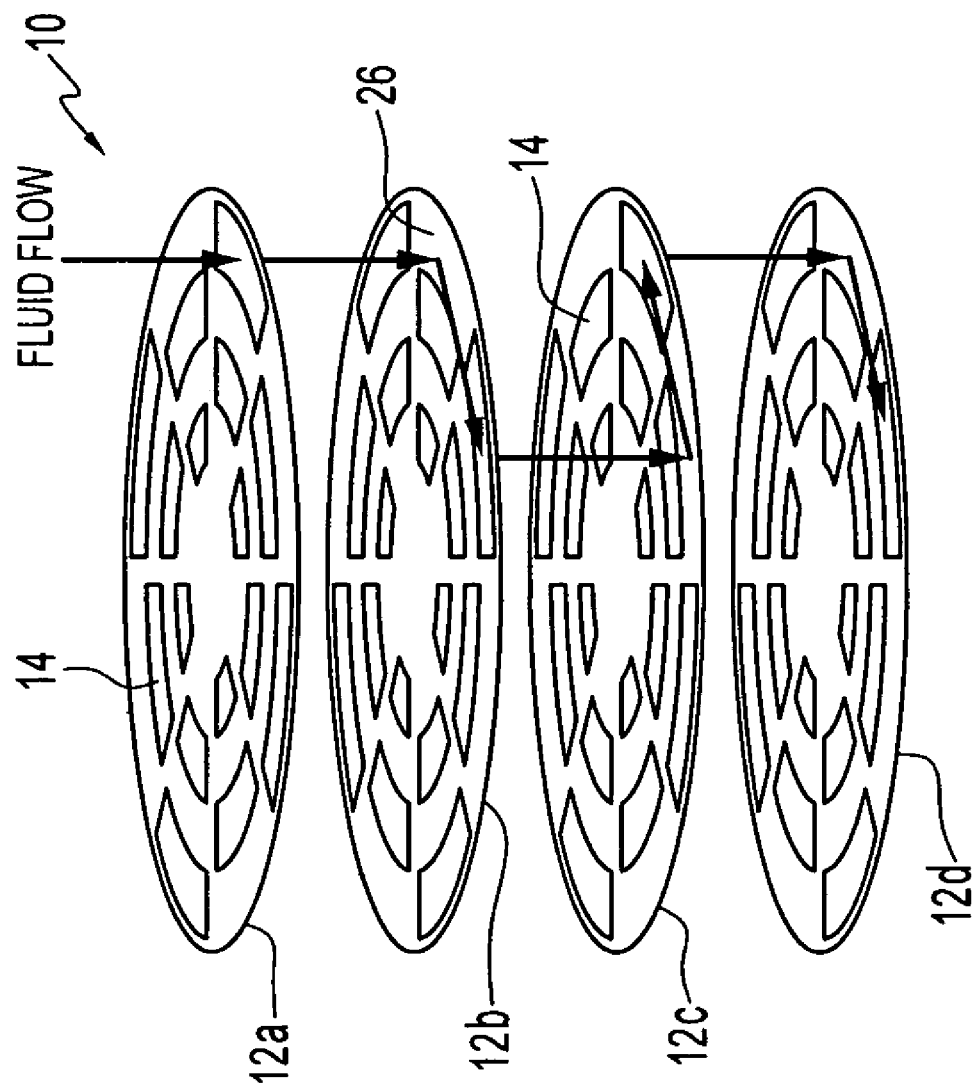
FIG. 1 is a schematic perspective view of a flow through micro scale sorbent plate array in accordance with an embodiment of the invention.

The invention concerns a collection device having a flow through micro scale plate arranged to collect analyte, and deliver a concentrated pulse of analyte to a detector system upon demand through heating. With the invention, analyte fluid flow is through at least one sorbent plate, which includes holes to pass analyte fluid flow, for example analyte vapor. Fluid flow for collection is generally perpendicular to the sorbent plate. Excellent interaction is achieved between the analyte fluid flow and a sorbent coating on the plate. After a period of collection, analyte may be provided to a detector system from the plate by heating the plate. Preferred embodiment plates include an integrated heater trace.

Embodiments of the invention use a series of two or more flow through micro scale plates. In preferred embodiments, a series of micro scale plates include a sorbent coating, and holes for analyte fluid flow through the plates. In preferred embodiments, individual plates in the series of plates are arranged so that at least some of the respective holes in the series of plates are at least partially aligned with a solid portion of another plate in the series of plates. In this way, a portion of fluid flow through a hole in one plate is initially brought into contact with a solid portion of a downstream plate before being redirected through a hole of the downstream plate. Embodiments of the invention including a series of flow-through plates are especially advantageous for collecting relatively volatile analyte compounds, which may bleed from sorbent material to a possibly significant extent even under ambient conditions. Downstream plates capture analyte that might bleed from a plate.

Other multiple and single micro scale plate embodiments also mitigate the potential for bleeding of relatively volatile analyte compounds. Having increased thickness of sorbent material on a plate or a zone of a plate can reduce analyte bleed. Forced cooling can also help. Coating both sides of the plates with sorbent material also improves the efficacy of collection and retention prior to desorption, as the collection fluid flows in embodiments of the invention bring analyte into contact with sorbent on both sides of the plate(s).

Collecting and concentrating an analyte with a collection device of the invention can mitigate issues associated with signal baseline drift. During thermal desorption of a concentrated analyte, a controlled temperature ramp can be employed to effectively desorb different types of analyte at different selected temperatures and improve the selectivity of the detector system. During a desorption cycle, if no analyte is detected, the signal baseline of the detector system may be reset.

Collection devices of the invention include multiple analyte embodiments. Using more than one sorbent in different sections of flow-through plates, either on a single plate or on multiple plates, allows a device of the invention to collect more than one type of analyte. In one embodiment, a single plate, which may or may not be part of a series of plates, includes multiple sorbent sections. In another embodiment, plates in a series of plates each include a single sorbent while the series of plates provides multiple sorbents by having at least one plate coated with a different sorbent than other plates in the series of plates.

Embodiments of the invention include both modular collection devices and stand alone analysis devices having a collection device and a detector system, e.g., a transducer, control circuitry, microprocessor, memory, pneumatic fluidics, a manifold and the like. Both modular collection devices and stand alone analysis devices of the invention may be highly compact. An example modular collection device unit can be made small enough, for example, to be conveniently worn on a person, affixed to a vehicle, inserted into the process flow of a machine in a production line, attached to plant life, portions of buildings, in ventilation systems, on cargo, on baggage, in baggage screening areas, etc. For example, a modular collection device of the invention might be clipped to a belt or clothing, or attached to clothing by a hook and loop fastener, e.g., Velcro®. In a method of use, such a device may be carried in an environment by a person to collect a sample, and then attached to a detector system after a period of collection. The same is true to a perhaps marginally lesser extent for stand alone analysis devices of the invention, depending upon the scale and type of the detector and detector system used. In an example, a highly compact and complete micro analytical device of the invention includes a chemresistor detector system in a MEMS integration with a collection device including flow through micro scale sorbent plates, a micro GC column, a power source, and electronics. The flow through micro scale sorbent plates of the invention permit very low pressure drops, and enable, for example, the use of inexpensive low power fans of the type used in laptop computers to generate high collection flow rates with very low power consumption. An example flow rate through a 6 mm square sorbent plate of the invention of 15 liters per minute may be generated from 250 milliwatts of power. An example very low pressure drop has a nominal value of about 0.15 mm Hg for a flow rate of 15 liters per minute.

Embodiments of the invention meet important design constraints imposed by considerations necessary for realization of practical self-contained portable micro analytical devices. These constraints include minimal power consumption for collection and desorption processes, low pressure drops enabling high fluid flow, a small physical footprint, and a robust mechanical design. A collection device of the invention enables construction of a micro analytical device that meets these constraints, and provides a short thermal time constant (e.g., one to hundreds of milliseconds) while reaching desorption temperatures, for example 100-200° C. By minimizing this period, the concentrated analyte pulse from the collection device arrives at the detector system with a high concentration amplitude over a short time period, to create a high overall signal to noise ratio.

Many other applications and operating conditions are possible. Additional features of the invention will be apparent to artisans in the following description of some preferred embodiments which will be described with reference to the drawings. Dimensions and illustrated devices may be exaggerated for purposes of illustration and understanding of the invention. The elements of the drawings are not necessarily to scale relative to one another. Schematic views will be understood by artisans as such views are commonly used in the art. Devices and arrays of the invention may be fabricated by processes well known to the semiconductor device and MEMS communities.

FIG. 1 shows an example flow through micro scale sorbent plate array 10. The array includes a plurality of plates 12, each of which includes a plurality of penetrating holes 14. The plates are arranged in a manner such that fluid flow encountering a first plate 12a cascades through the plate array from the first plate and then continuing through to a last plate 12d. Though the plates 12 in the plate array 10 are shown as being parallel to each other, a parallel configuration is not required and in certain instances a non parallel or tilted configuration may be advantageous. A substantially parallel arrangement is preferred, however, for most applications. In preferred configurations, analyte fluid flow encounters the plates in a direction substantially perpendicular to the surface of the plates 12, where it is sorbed by the sorbent coating on solid portions of the plates 12. The fluid flow is directed into solid portions of the plates and circulated over the solid portions, while being redirected through the penetrating holes 14. Continuing downstream to a next plate 12b in the plate array 10, fluid flow proceeds in a similar manner. Excellent interaction between the analyte fluid and the sorbent coating is realized. In addition, high flow rates of analyte fluid flow may be employed.

The plates 12 may have a minimal thickness necessary for fabrication processing and for structural integrity during assembly and use. The plates 12 must withstand contemplated fluid flows, and the stresses induced by the fluid flow variations and temperature fluctuations introduced during the collection and desorption of analyte. Plates of the invention may be made very small, both in diameter and in thickness. An example plate may have a 1-10 mm diameter, for example, and may have a thickness from a few micrometers to hundreds of micrometers or more. Basic and complex geometric shapes are possible. Plates and plate arrays may also be operated in parallel, for example to divide a massive fluid flow among multiple plate arrays for sampling and analyte collection. Small thicknesses are preferred to provide low thermal mass and pressure drop, as the low thermal mass enables a rapid desorption temperature ramp to be realized, and low pressure drop allows high flows with minimal power usage. Embodiments of the invention provide a short thermal time constant (e.g., 1's-100's ms) while reaching high desorption temperatures, for example 100-500° C. By minimizing this period, the concentrated analyte pulse arrives at the detector system with a high amplitude over a short time period, to create a high overall signal to noise ratio. A preferred strategy for desorbing in an array like that shown in FIG. 1 involves serial desorption through the array. The strategy for desorbing collected analyte proceeds by synchronizing heating of the planes with the flow of the resulting analyte plug through the array.

Figure 2B:
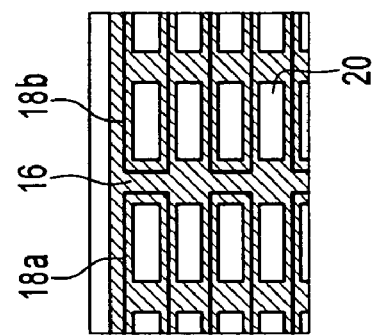
FIGS. 2A and 2B are respectively a top view and a partial enlarged top view of a prototype flow through plate in accordance with an embodiment of the invention.
Figure 2A:
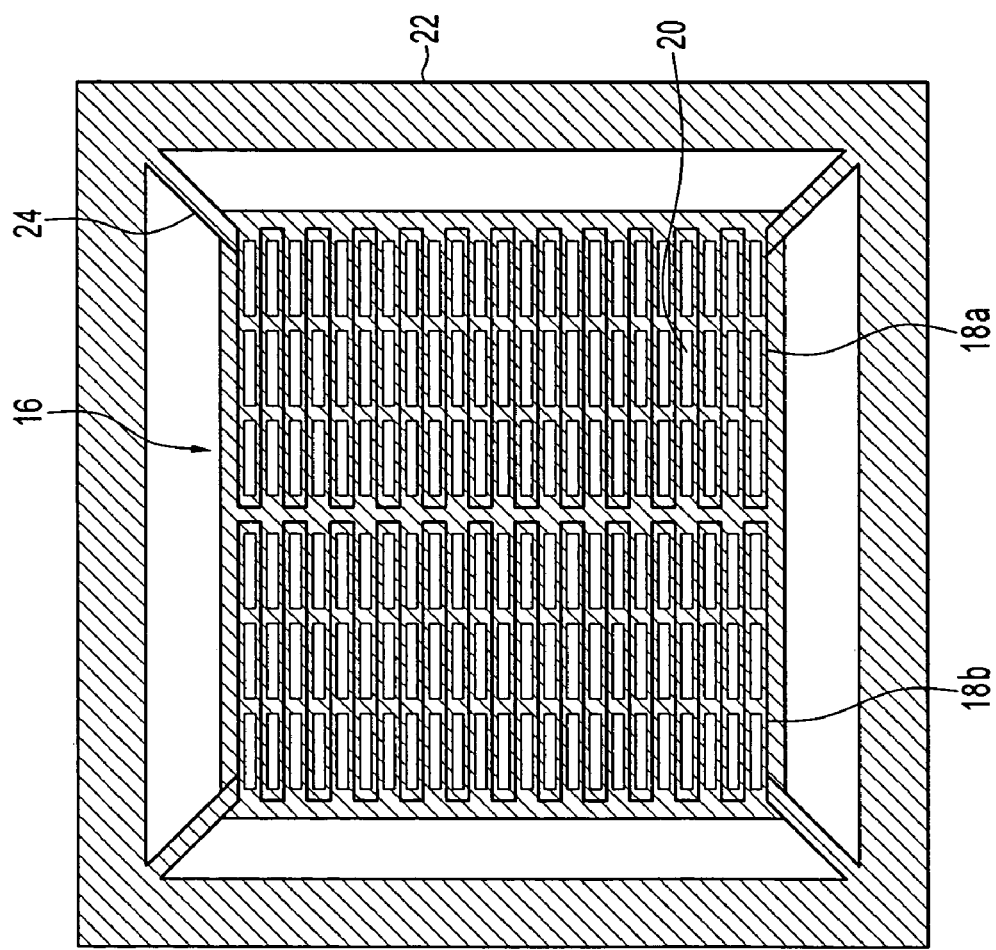

We have conducted tests on prototypes consistent with the plates 12 shown in the plate array 10 of FIG. 1. We tested a prototype silicon-polyimide coated plate 16 with an active area of ~6 mm×~6 mm and a plate thickness of ~5.6 μm. The prototype plate 16 is shown FIGS. 2A and 2B. In addition, FIGS. 2A and 2B illustrate an integrated heater 18. The heater 18 is a trace of conductive material, and forms a resistive heating element.

In the embodiment shown in FIGS. 2A and 2B, the plate includes two heater traces 18a and 18b. Use of separate heater traces allows desorption to be zoned. This is useful, for example, in embodiments of the invention that use different sorbents in different zones. It is also useful in embodiments of the invention where it is desirable to be conducting collection in one zone, while conducting desorption in another zone.

In the experiments, the heater 18 was formed of Pt, ~35Å wide and ~1650Å thick. The Pt was deposited over ~200ÅCr, which aided adhesion. Generally, materials that are preferable for heater traces are materials having a high electrical resistivity and low thermal conductivity. Platinum, tungsten, and other refractory metals and alloys have high temperature coefficients of resistance, and will induce the rapid heating effect that is desirable. Holes 20 in the prototype of FIGS. 2A and 2B are best seen in FIG. 2B, which is an enlarged image of a portion of the FIG. 2A device. The holes 20 occupied about half of the surface area of the plate. The plate 16 was formed from a silicon wafer coated with polyimide and was ~5.6μm thick. It was supported by a silicon frame 22 and polyimide suspension arms 24. Materials and dimensions are provided so that the tests may be understood, and as an example embodiment of the invention. Prototype plates have also been fabricated in uncoated silicon, and these plates were found to be more fragile. Uncoated silicon and other materials less rigid than the polyimide coated silicon may be used, but in cases where the ratio of holes to solid portions is high or the plate thickness is minimized, a coating of polyimide or another support material is helpful. Other materials include all materials that are amenable to micro fabrication processing, and suitable for the conditions of operation.

Figure 3:
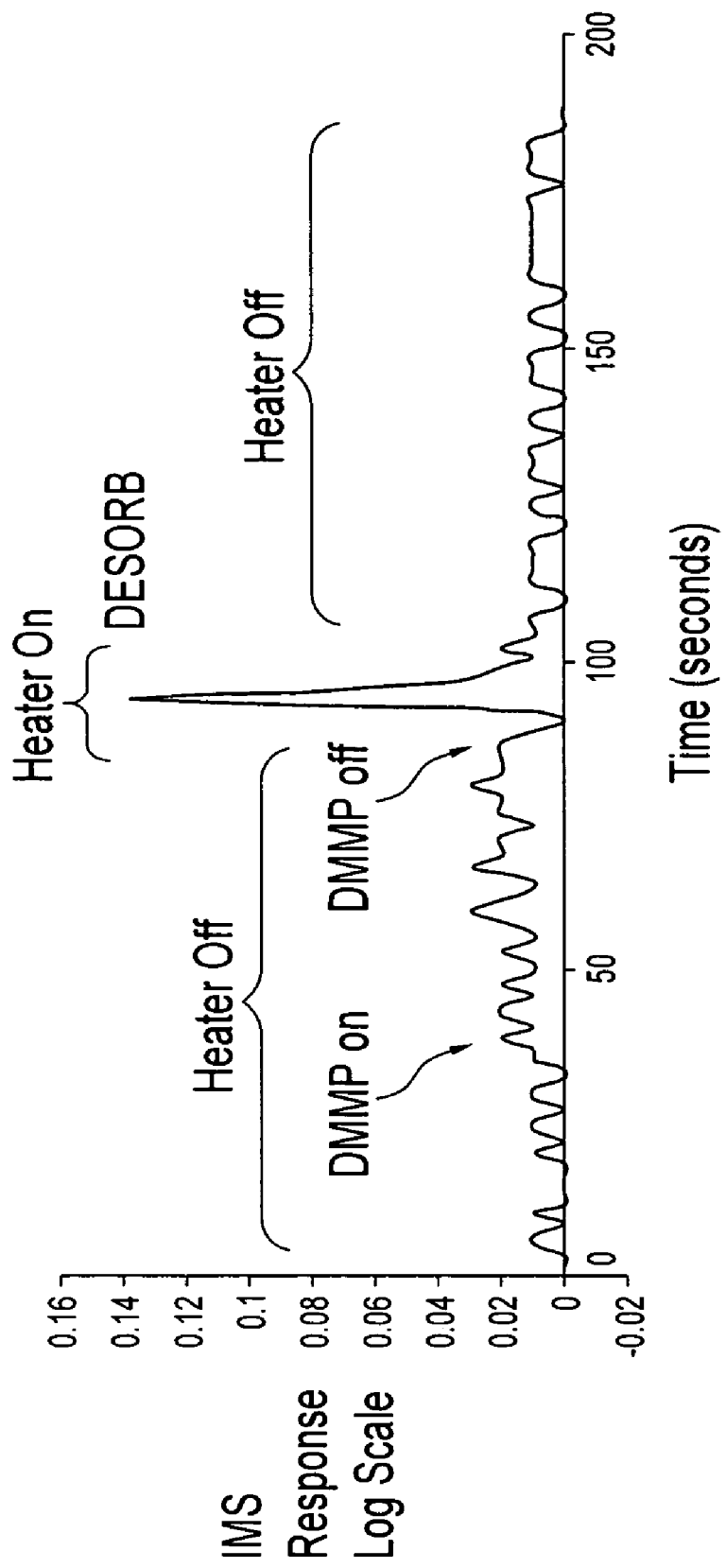
FIG. 3 is a graph of data showing the sensitivity gain of the FIGS. 2A and 2B prototype.
Figure 10C:
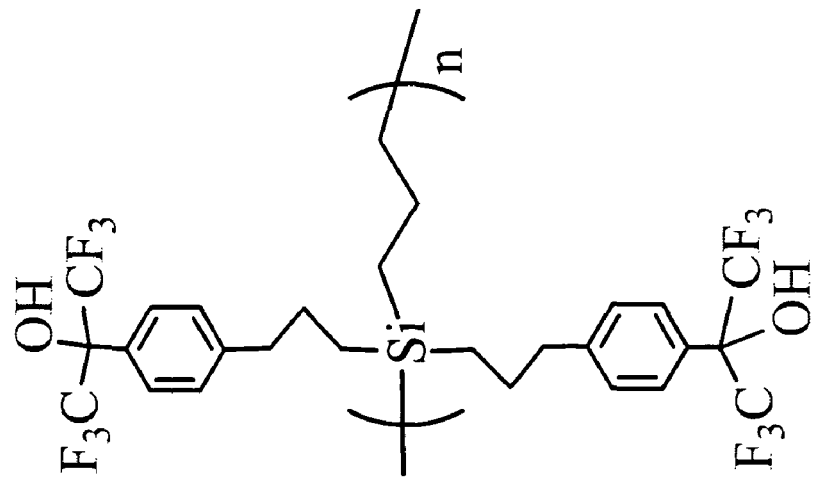
FIGS. 10A-10D illustrate representative coatings for the sorption of hydrogen bond basic and dipolar analytes.
Figure 10B:
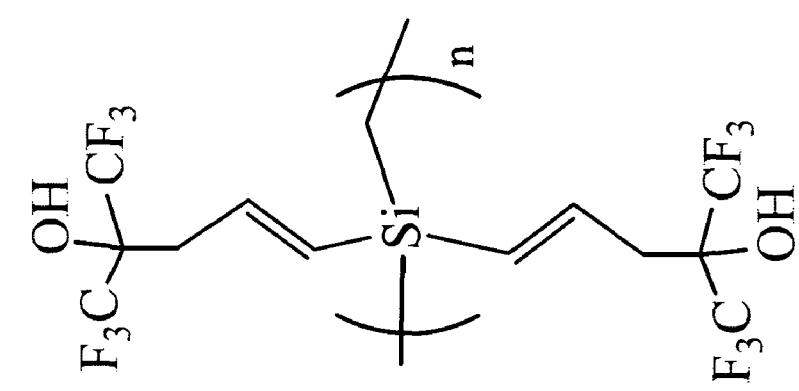
Figure 10A:
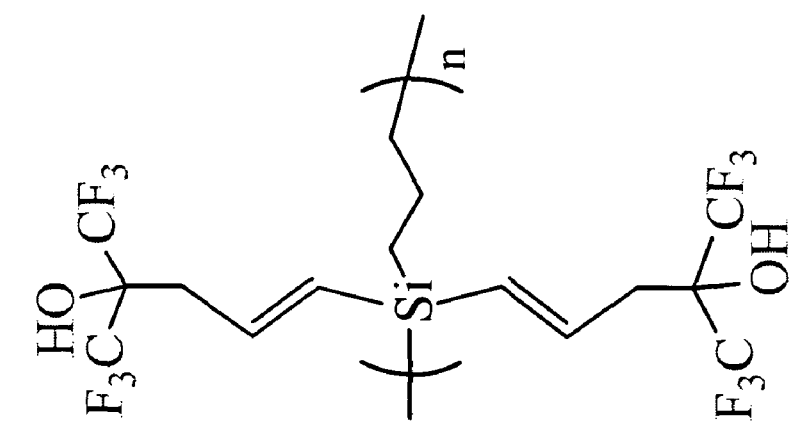
Figure 10D:
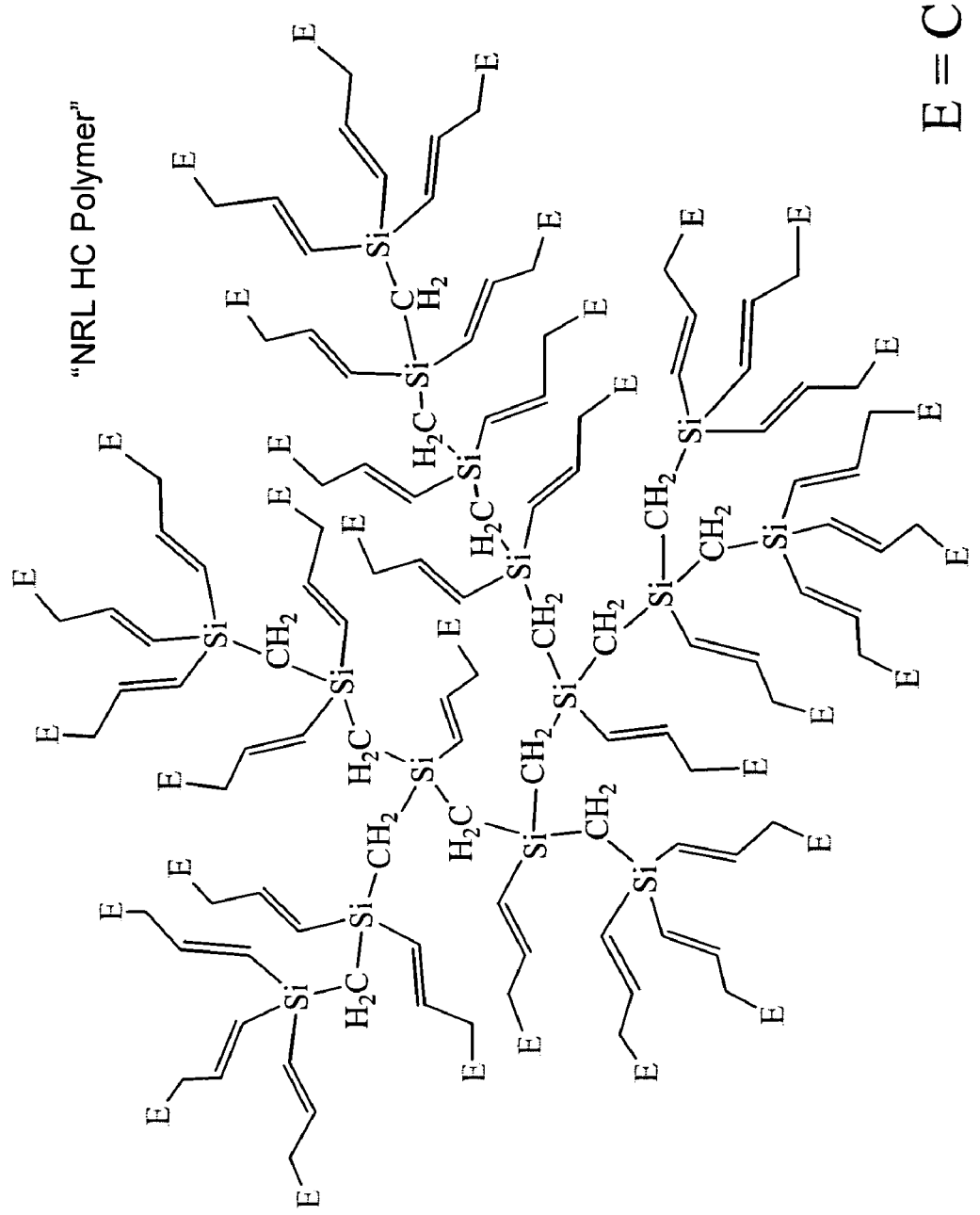

The prototype of FIGS. 2A and 2B has been tested with 30V applied to the heaters. The transient data were fit to an exponential decay, given by $y = y_o + A_1 e^{-(x-x_o)/t_1}$, and yielded a time constant of 104 ms. At 150° C. the device required approximately 200 mW. During testing, very high collection efficiencies were realized for the nerve agent stimulant, dimethylmethylphosphonate (DMMP). The sorbent coating used was an NRL "HC" polymer shown in FIG. 10D. Measurements on the non-optimized prototypes were taken with a hand held Ion Mobility Spectrometer (IMS) detector system. The sensitivity gain results observed were in the region of multiple orders of magnitude. This is shown in FIG. 3, where a small time period pulse of concentrated analyte is apparent at about 90 seconds on the time scale. This is when the resistive heating element was turned on, immediately following a time when a source of DMMP being collected by the plate was turned off. During collection, beginning at about 35 seconds, the resistive heating element is off. Thousands of thermal desorption cycles produced no degradation in device performance.

In an array of plates, like that in FIG. 1, or on a single plate like that shown in FIGS. 2A and 2B, the type of sorbent coating on the plates determines what analyte will be selectively trapped. Each plate may also include more than one type of sorbent coating to create different active sites on a single plate. In other embodiments each plate includes a single type of sorbent, while one or more other plates in an array have a different type of sorbent.

Figure 4:
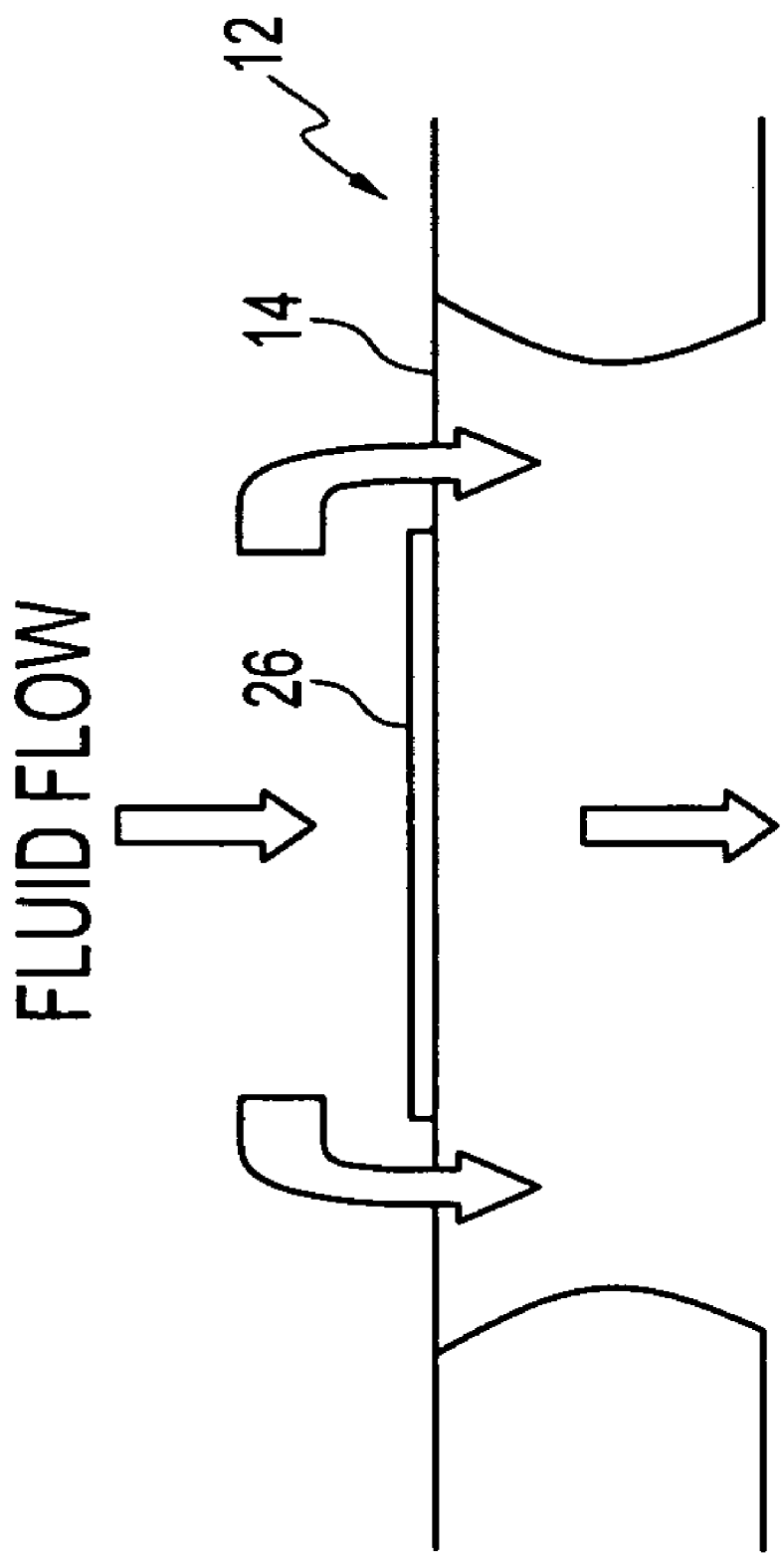
FIG. 4 schematically illustrates analyte fluid flow through a plate of the invention.

FIGS. 1 and 4 illustrate analyte fluid flow and interaction with a flow through micro scale sorbent plate 12 of the invention. The fluid flow, illustrated by arrows in both figures, follows a cascading path in a plate array of the invention, as shown in FIG. 1. A cascading flow is achieved by intentional misalignment between holes 14 in the array. At least some of the holes 14 in one plate are aligned, partially or completely, with solid portions of a downstream plate. Accordingly, as illustrated in FIG. 4, a large portion of fluid flow first encounters a solid portion 26 of a plate 12, and is redirected over the plate through a hole 14. Replicated in an array including more than two plates produces a cascading effect, with analyte encountering sorbent on solid plate portions in a manner providing excellent interaction between the sorbent and the analyte in the fluid flow.

The arrangement of plates into arrays, and with particular alignments may be accomplished either by direct bonding of plates to other plates, or by first affixing plates to carriers and then bonding the carriers together. A specific misalignment between holes in adjacent plates can provide the cascade effect illustrated in FIG. 1. As a first example, finished plates may be bonded directly together with an adhesive. A first plate is bonded to a multipin, e.g. 48 pins, package that is capable of providing electrical connections for the array. Subsequent devices are rotated by 90° and adhered by pipetting an epoxy on to the die below. Of course, there are a number of alternatives for the die adhesion mechanism. These might include techniques used in flip-chip, anodic, or eutectic bonding. By using a flip-chip bonder and associated alignment capabilities one can accurately place the die so that perforations in the downstream plate do not overlap with the previous one. A bond is formed with either ultrasonic or compressive forces that compress bump-pads placed on the bottom plate with a wire bonder. This process usually requires a ball-bonder to produce the rounded gold or aluminum pads from wire.

In a second example, finished plates are first bonded to a custom package such as a PC board using conventional wire bonding and packaging techniques. Then the packages are stacked on top of one another. A hole in the PC board allows for analyte passage to downstream planes. This example has the advantage that flow channels might be incorporated within the plane of the package to facilitate moving analyte to other components.

With regard to a single plate, large parts of fluid flow first encounter solid portions of the plate before being directed through the holes. Analyte-sorbent interaction is much improved than in flow over devices. A flow through plate or an array of the invention can selectively trap analyte(s) of interest and thermally desorb and deliver a narrow time width pulse of concentrated analyte into a narrow orifice intake. Plates and arrays of the invention provide an extremely low-pressure drop, to allow a high flow to be passed through the device and intimately contact the majority of the collection surface, with the minimum power expended. The ratio of solid plate portions to holes influences analyte collection efficiency, air flow and pressure drop. The number of plates in an array also influences the same parameters. These parameters may be optimized for particular applications. An example ratio of solid portions to holes is 1:1, i.e., 50% of the solid plate portions have been etched through to form penetrating holes. Other example embodiments have holes occupying a larger or smaller surface area.

The ratio of solid portions to holes may be determined in a particular design depending upon a number of factors, including, for example: permitted pressure drop, the materials used to form the plates, and the number of plates used in an array. We note that as the percentage of hole area increases, the plates become more fragile and less sorbent while the pressure drop decreases. Also, as the percentage of hole area decreases, sorption increases due to the increase in available active sites and the plates are less fragile, but the pressure drop increases. When optimizing a particular design, the negative effects of increasing or decreasing hole area may be tempered by selecting appropriate materials and/or dimensions. For example, silicon is fragile for very thin plates and where hole area becomes very large, but the fragility may be overcome by a support coating or a more robust material such as silicon carbide or silicon nitride. Preferred embodiments of the invention include plates having a hole surface area of ~40-60%, while other optimizations of the invention include larger and smaller hole surface areas.

Figure 5:
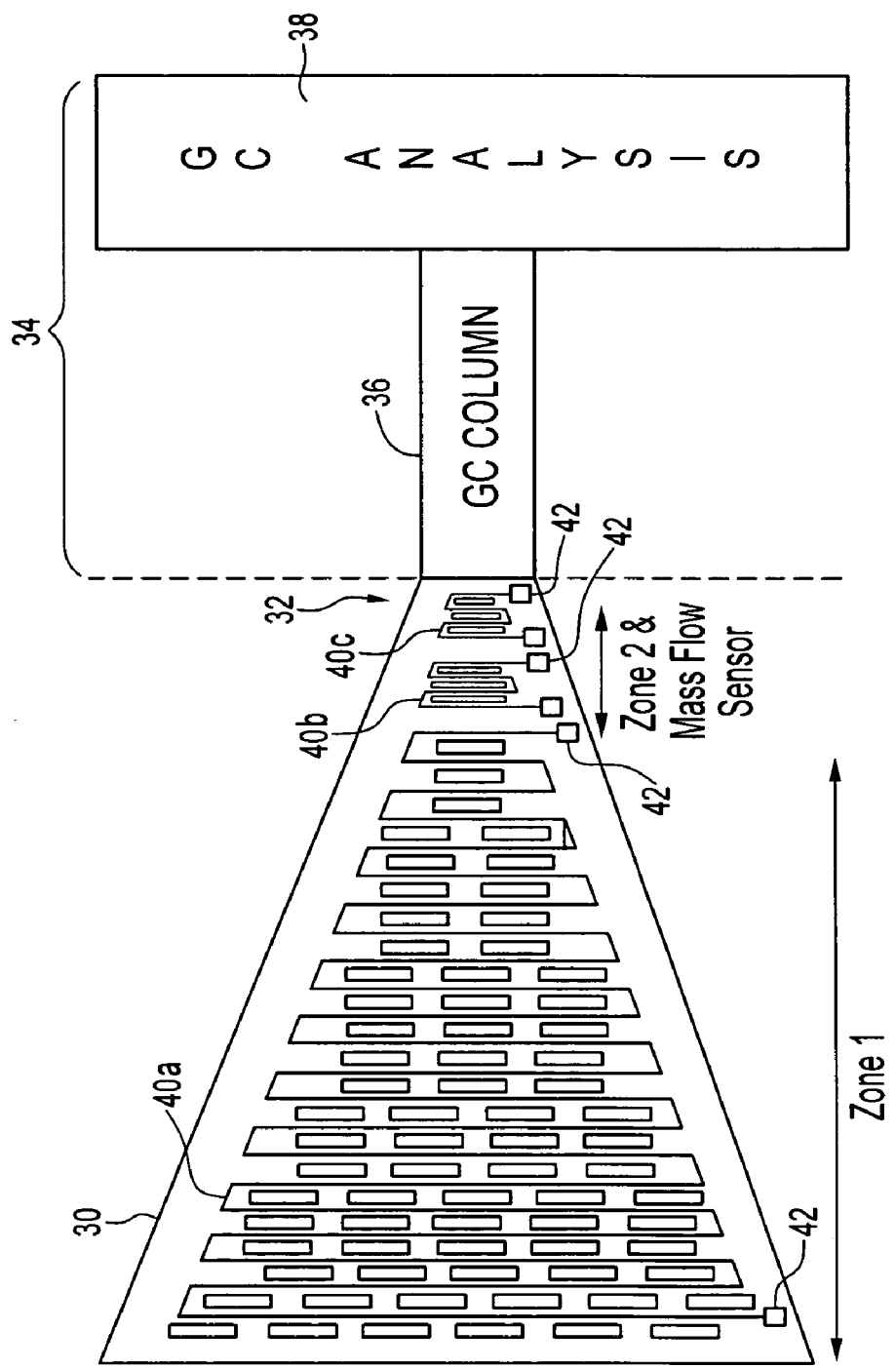
FIG. 5 is a schematic top view of a flow through micro scale sorbent plate and analyte collection and analysis system in accordance with another embodiment of the invention.

FIG. 5 shows another example micro scale plate 30, having a geometry including a tapered shape and a narrow end 32. In exemplary embodiments, the narrowed end 32 is sized to match an inlet of a detector system 34. The analysis and detector system in FIG. 5 is a gas chromatography system, and the narrowed end interfaces with the gas chromatography (GC) column 36 that serves as an inlet to a GC analysis section 38. This permits a low loss transfer of analyte into the detector system 34. The detector system 34 may be, for example, a micro machined or conventional capillary gas chromatographic column. Other detector systems include, for example, a narrow orifice inlet or membrane interface to a micro machined or conventional mass spectrometer, or a micro sensor pneumatic manifold opening.

The small inlets of many detector systems present an interface challenge that is met by the device of FIG. 5. If there is a mismatch to the inlet of the detector system, the efficiency realized by the concentrated analyte pulse that may be delivered by a collection plate or plate array of the invention is tempered by the inefficiency in transferring analyte into the detector system.

Another challenge is the limited flows tolerated by the detector system. Preferred embodiments of the invention have a high collection flow, but that flow cannot always be transferred into the detector system. For example, a limited conductance 100 µm wide gas chromatography column may have a flow rate at the opening of only 10's of ml/min. This flow rate is insufficient to overcome diffusion of analyte as it is desorbed from the surface of the plate or plate array.

In a preferred method of the invention, a device of FIG. 5 is used with two flows. This also forms the basis for methods of the invention with respect to FIG. 1. A collection flow is as illustrated in FIGS. 1 and 4, namely, substantially perpendicular to the surface of the plate(s). High flows are possible, as the exit for such substantially perpendicular flows is not into a detector system. In embodiments of the invention, the exit collection flow is treated and released into the environment. In other embodiments, it is collected or stored. In still other embodiments it is fed back into the input flow stream to capture analyte that may not have been collected in a first pass. An analyte pulse is then delivered during desorption by a low flow that is generally parallel to the surface of the plates. The direction of the parallel low flow in FIG. 5 is toward the narrowed end 32 and into the GC column 36, while the direction of perpendicular flow is into or out of the page.

The plate 30 in FIG. 5 also includes a plurality of heater traces 40a, 40b, and 40c. The traces 40a, 40b, 40c, divide the plate into different zones, labeled zone 1 and zone 2. Zone 1 is a collection zone, and zone 2 is a delivery zone. Electrodes 42 are illustrated as contacts to the heater traces, and may be used to interface the plate 42 with control electronics. The primary trace 40a, defines zone 1 and the primary collection area exposed to high flows during collection. In a preferred embodiment using ambient temperature sorbent coatings, during collection, the heater trace 40a is off. After a period of collection, zone 1 is heated and zone 2 is left at ambient temperature. In a preferred embodiment, the plate portion in zone 2 is covered in a thicker layer of sorbent polymer. This permits a larger amount of analyte collected in zone 1 to be transferred to the smaller zone 2. The active area of zone 2 is narrowed so that it has dimensions comparable to and is immediately adjacent to the entrance of the GC column 36. Thus, the FIG. 5 device may efficiently transfer analyte into the GC column during desorption induced by exciting the heater traces 40b, 40c in zone 2. At the same time, a larger surface area in zone 1 provides for efficient collection.

While two zones are illustrated, there may be many heated zones and variable width heater traces to control the thermal distribution. A vacuum style pump that is pneumatically connected to the narrowed end 32 may be used to transfer analyte to zone 2 from zone 1. Once analyte has been loaded into the next stage of the analyzer system (e.g. GC column, micro sensor, mass spectrometer), the heaters in zone 2 can be used as a mass flow sensor.

The heater traces 40a, 40b, and 40c may also comprise segmented heaters so that after collection of analyte, the majority of the device can be heated while holding a smaller section at ambient collection temperatures. Analyte is allowed to migrate from the heated areas to the cool areas. Collection of analyte on the unheated segments allows the analyte to be focused onto a smaller area that is positioned opposite to a narrow orifice. The size of the analyte focused segment is designed to be comparable with the size of the orifice into which analyte is intended to be delivered. Thicker layers of sorbent polymer can be used on the analyte focusing segments to avoid overloading issues. In order to speed the redistribution of analyte, the pump that was used to collect analyte or another lower flow rate pump can be operated in a rapidly changing forward and reverse airflow mode, to allow turbulent airflow to wash forward and backwards through the plate(s). In this mode of operating, the collection flows and final desorption flow into a narrow orifice can be maintained in the same direction, flowing normal to the collection surface and through the pores in the surface. Alternatively, the plate(s) can be isolated after analyte collection and thermally desorbed as described above so that a small area is left at ambient temperatures (or actively cooled) so that analyte redistributes to a relatively small zone. Isolation can be achieved by suitable valving.

Plates and arrays of the invention may be fabricated by different MEMS and semiconductor fabrication techniques. They also may be packaged in different ways, and placed into flow systems including valves, pumps, and even fans. The low pressure drops enabled by the plates and arrays of the invention permit high collection flows from inexpensive low power fans, such as those used in laptop computers.

An example plate fabrication process begins with depositing a 0.1 µm layer of aluminum onto an oxidized (100) silicon wafer. The aluminum is patterned to form a thermal distribution plate on the back of the wafer and the oxide is used as a stop layer for Deep Reactive Ion Etching. Polyimide (PI 2611 from HD Microsystems) is then spin coated to a thickness of ~3-6 µm. Since oxygen plasma is used to etch the polyimide it is necessary to use a metal masking layer instead of photoresist for patterning. Therefore, aluminum is sputter deposited and patterned to produce apertures for the flow through of analyte. The polyimide is etched using oxygen in a capacitively coupled Reactive Ion Etcher. The aluminum is then removed and Cr/Pt electrodes are fabricated using a lift-off technique. Next, a negative photoresist is spun on to both sides of the wafer with a nominal thickness of 6-7 µm. Etch windows are patterned on the back and the front of the wafer is exposed without a mask in order to leave a protective layer for dicing. The silicon dioxide exposed by the windows is removed in a buffered oxide etch (BOE) and the wafer is diced. The hotplate die are adhered to a resist coated handle wafer using silver vacuum grease and etched using DRIE. The front oxide is used as a stop layer and prevents damage to the polyimide. Finally the oxide is etched from the back of the die using hydrofluoric acid and the prototypes are removed from the handle wafer and cleaned.

Sorbent coatings may be applied by a number of techniques, and the particular application method may depend upon the type of sorbent coating. Dip coating is one technique. A flow through plate is prepared for bonding of the sorbent, which may involve cleaning and drying, for example. It is then dipped into a solution of the sorbent coating. Other techniques include, for example, aerosolized coating, syringe coating, inkjet coating, laser evaporation, spin coating and washing sorbent solution over a flow through plate.

Figure 6:
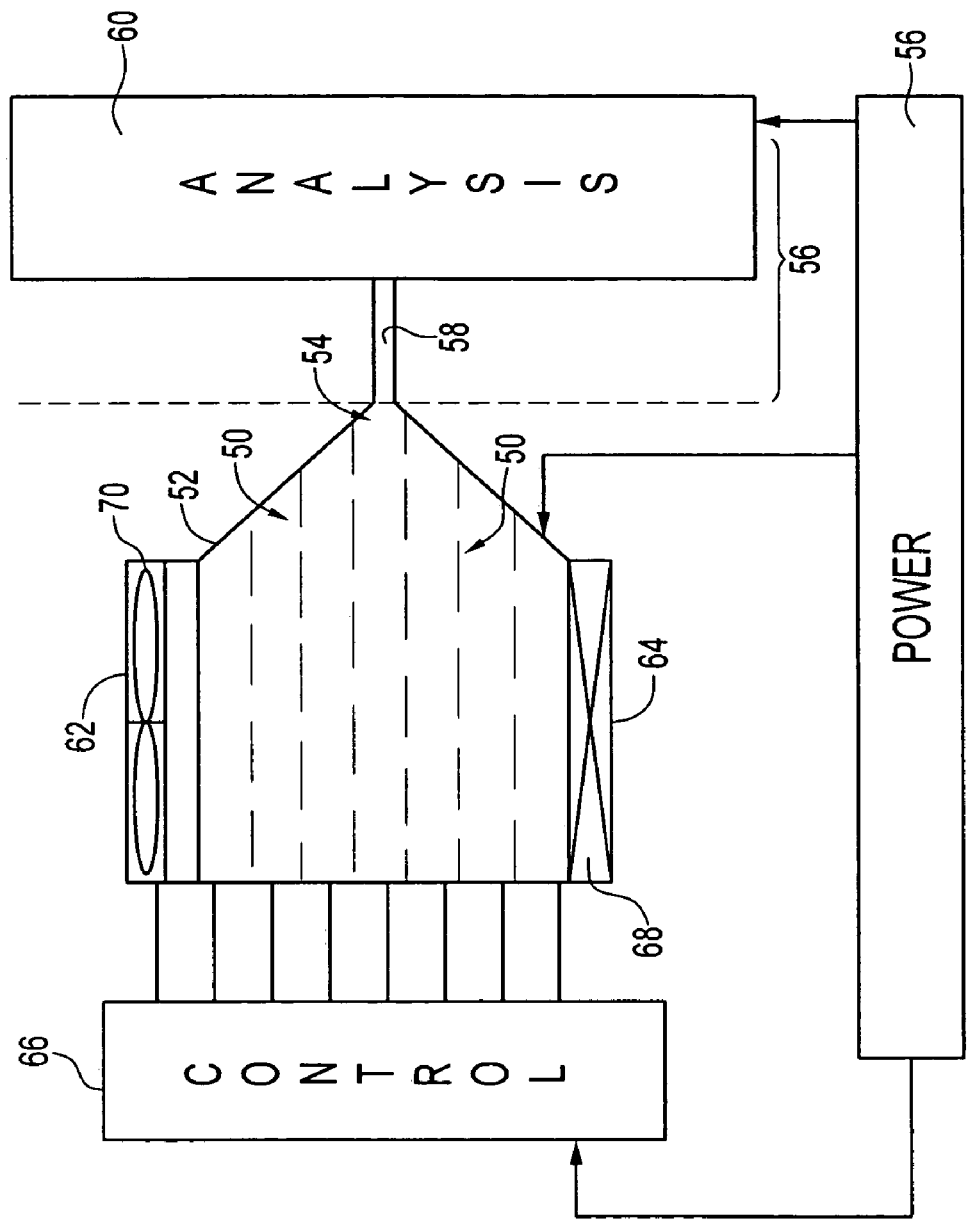
FIG. 6 is a schematic diagram of an analyte collection and analysis system in accordance with an embodiment of the invention.

An analyte collection and analysis system is shown in FIG. 6. The system includes an array of micro scale sorbent coated flow-through plates 50 enclosed in a housing 52. The plates 50 are preferably arranged to induce the cascading flow shown in FIG. 1, and have a narrowed end 54 to interface with a detector system 56 having a column 58 and analysis section 60 in accordance with FIG. 5. A collection inlet 62 for analyte fluid flow receives, fluid flow, e.g., gases, liquids, or solids, and the housing 52 directs the fluid flow through the array. An outlet 64 permits high flows to be directed out of the housing 52 and away from the detector system 56 during periods of analyte collection and concentration in the array. The internal walls of the housing 52 should be inert to the analyte of interest, either because of material properties or by active heating of the internal surface to avoid sorption. A controller 66 controls an airflow system that includes a valve 68 for the outlet 64 and a low power fan 70. A power source 72 powers the system.

During a period of collection, the outlet is open and the fan 70 is provided power to induce a high cascading flow through the array of plates 50. After a period of collecting and concentrating analyte in the array, analysis is conducted by the detector system 56, which is provided a concentrated analyte pulse by the array. The detector system 56 tolerates lower flows. The controller 66 closes the valve 68 and reduces the power to the fan 70. With some detector systems, there will be no need to induce flow during analysis by a fan or other means, as the detector systems provide for some flow. Closing of the outlet 64 changes the air path from a cascading path primarily through the array to a primarily parallel path across the plates 50 and into the detector system 56.

The physical configuration of the housing 52 and the detector system 56 may be highly compact for a self-contained field analysis device. In other cases, the housing 52 may be detachable from the detector system 56, and might include a carrier aid, such as a handle or clip. The overall dimensions of the housing 52 may be such that the housing may be conveniently carried on the body of a person, for example.

For particular analytes of interest, devices of the invention may be optimized. Artisans will recognize various parameters and operational conditions from the above description of exemplary devices that can be tailored to optimize concentration and delivery of a particular analyte of interest. As examples, the operating temperature range, sorbent coating thickness, flow volumes, etc. can be tailored to meet specific optimizations.

Figure 7A:
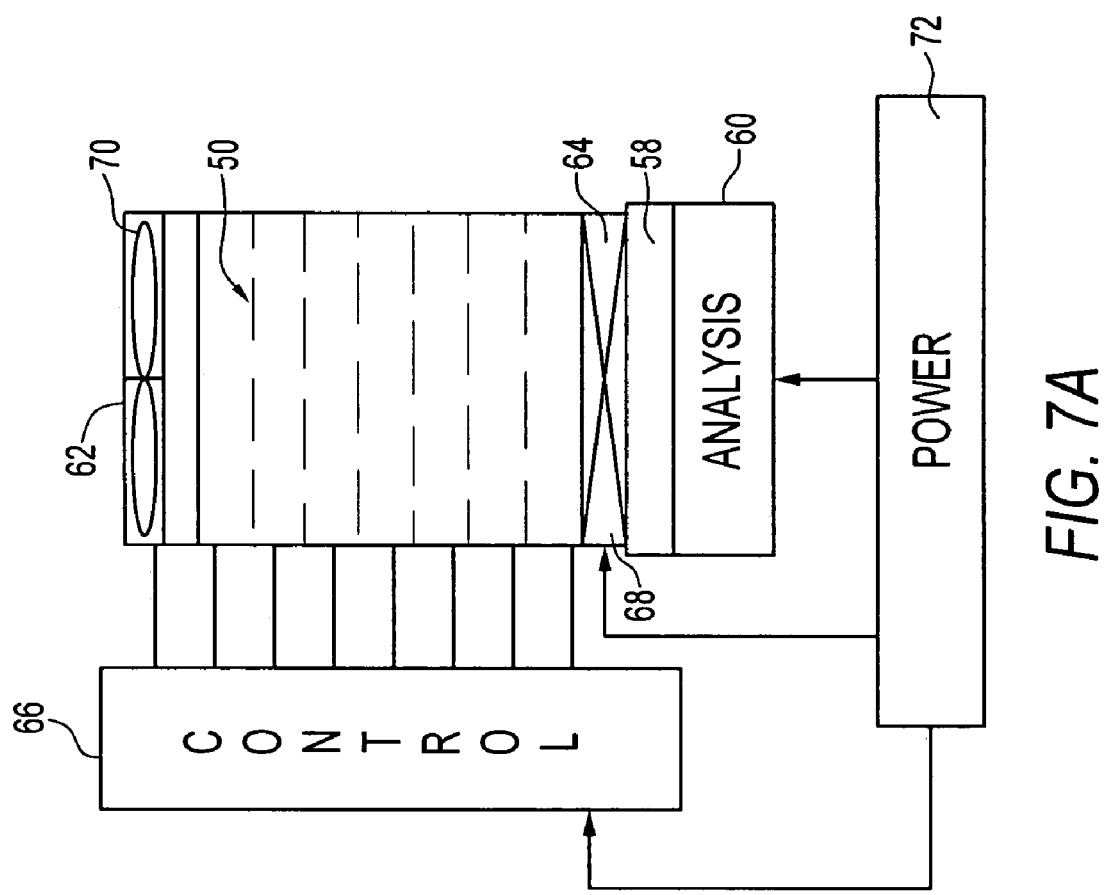
FIG. 7A is a schematic diagram of an analyte collection and analysis system in accordance with another embodiment of the invention.

FIG. 7A shows an analyte collection and analysis system in accordance with another embodiment of the invention. The system of FIG. 7A is similar to the system of FIG. 6, and like reference numerals are used for like parts. In FIG. 7A the plates 50 are formed in accordance with FIG. 1, and the system uses a vertical flow for both collection and desorption. The analysis section 60 interfaces with the outlet 64. Collection flows may still be high. In one case, the analysis section 60 may be the type of device that can tolerate high flows. In another case, the outlet 64 includes a flow bypass, such as openings that permit flow to be directed into the environment. The openings may be closed during desorption to direct a low flow into the analysis section 60.

Figure 7B:
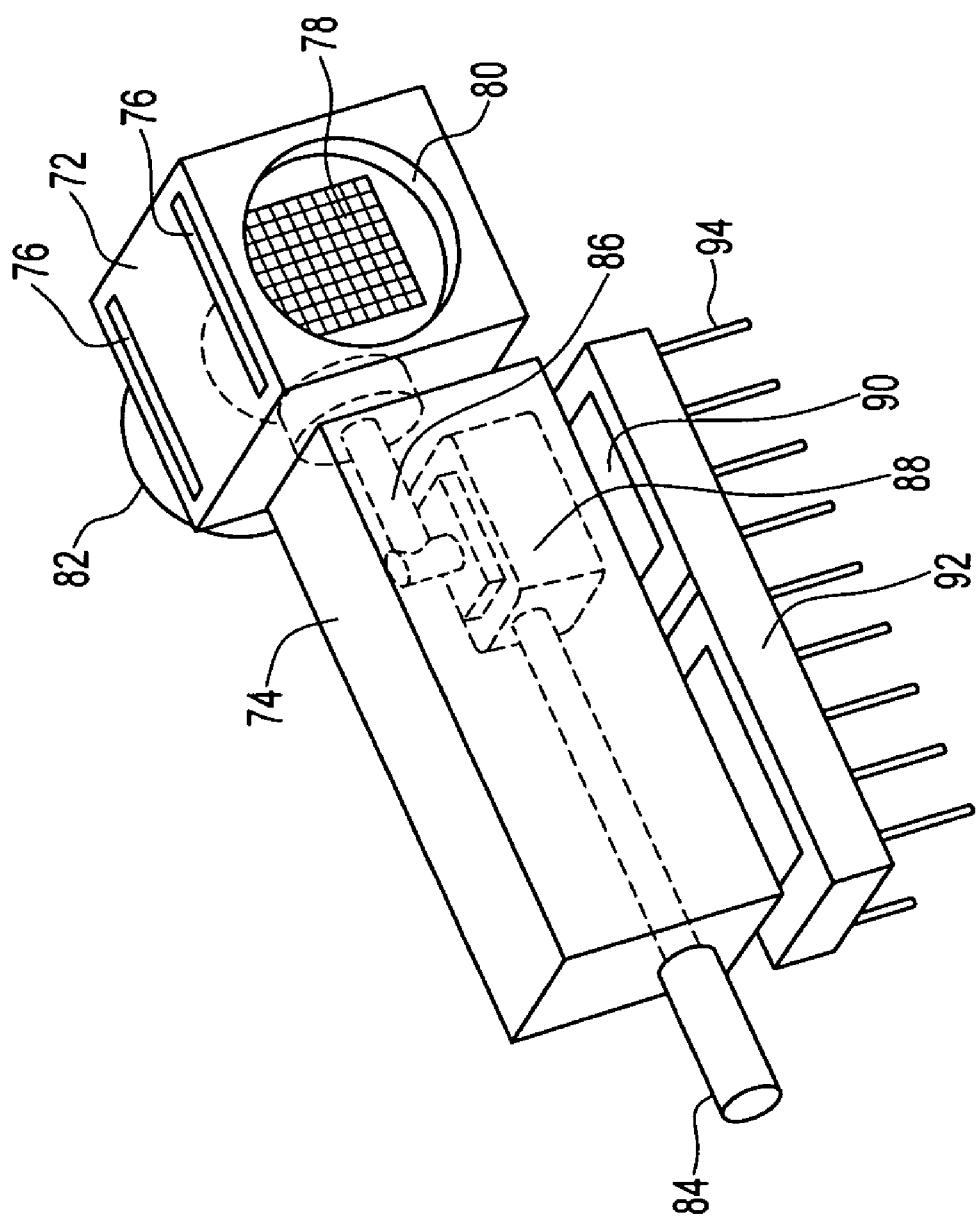
FIG. 7B is a perspective and partially transparent schematic view of an analyte collection and analysis system in accordance with another embodiment of the invention.

FIG. 7B shows an analyte collection system in accordance with yet another embodiment of the invention. The system includes a collection housing 72 and an analysis housing 74. Slots 76 in the collection housing 72 accept micro scale flow through sorbent plates 78 of the invention and hold them in place. The slots 76 permit plates 78 to be changed, while in other embodiments the slots may be omitted and the plates may be permanently affixed or otherwise temporarily affixed in the collection housing 72. Collection flow is generally perpendicular to the plates in a direction entering through an opening 80 and exiting out through another opening 82, which may include a fan to induce the collection flow. During desorption, the fan is turned off and a pump 84 draws in low flow from both openings 80, 82 and in through and across the plates 80 into a duct 86 in the analysis housing. A hood 88 brings concentrated analyte into contact with sensors 90 on an integrated sensor and controller chip 92, which is shown in exploded fashion but is connected to the analysis housing 74 such that the hood 88 seals over the sensors 90. The integrated sensor and controller chip 92 is shown with pins 94 to connect to other circuitry.

Figure 7C:
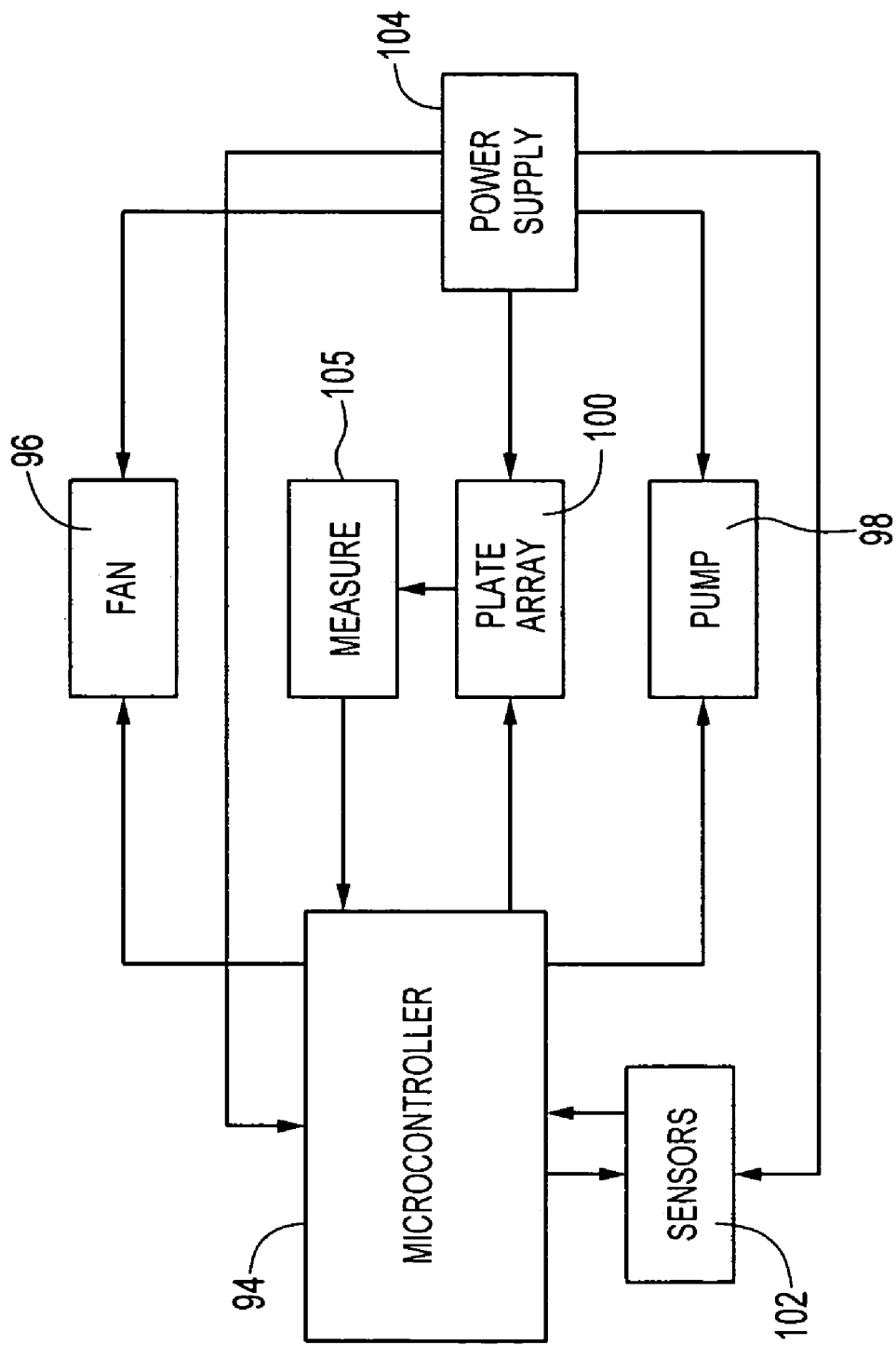
FIG. 7C is a block circuit diagram for an analyte collection and analysis system in accordance with an embodiment of the invention.

Circuitry for an analysis and control system such as that shown in FIGS. 7A and 7B is shown in FIG. 7C. A microcontroller 94 runs the system. It directs a fan 96 for inducing collection flows, and a pump 98 for inducing desorption flows. The microcontroller 94 controls the heating of plates in a plate array 100 and the operation of sensors 102. In the case of multiple traces, as in FIG. 2A and FIG. 5, the microcontroller 94 preferably controls each heater trace independently. The microcontroller 94 may embody or access memory for sensor data and analysis. The system is powered by a power supply 104.

The microcontroller 94 may also receive a feedback signal from a measuring circuit 105. In a preferred embodiment, the microcontroller drives resistive trace heating elements with a pulse width modulation (PWM) signal consisting of on and off pulses of variable width. During the off times of the PWM signal, the heating element is switched into the measuring circuit 105, for example a Wheatstone bridge. The microcontroller 94 determines plate temperature from the feedback. Since the resistive heating element preferably has a high temperature coefficient of resistance, it can be used as a temperature sensor itself, saving valuable space that would be required for a separate temperature transducer, which would also reduce the power available to the resistive heating traces. Based upon the feedback, the microcontroller 94 can adjust the pulse width of the PWM driving signal to adjust temperature or maintain temperature at a desired level. Feedback and control can be used to regulate temperature and ensure, for example, that the sorptive material coatings on the plates or the heating elements are not damaged.

As heating elements are preferably individually controlled, the microcontroller 94 may, for example, desorb different plates or different zones (discussed above), perhaps having different sorbent materials, at different times to enhance selectivity of the detector system. The microcontroller 94 may also ramp the temperature of a heating element to create a chromatographic effect to increase selectivity of the detector system. The microcontroller 94 may also control the fan or pump or other fluid flow inducing device during desorption to reduce its cooling effect on the heating element during desorption. This measurement approach can also be used to perform built-in-tests and in-circuit calibration. Diagnostics can also be performed by comparing historical data of thermal time constants to determine if the fluid flow has become blocked.

Figure 8:
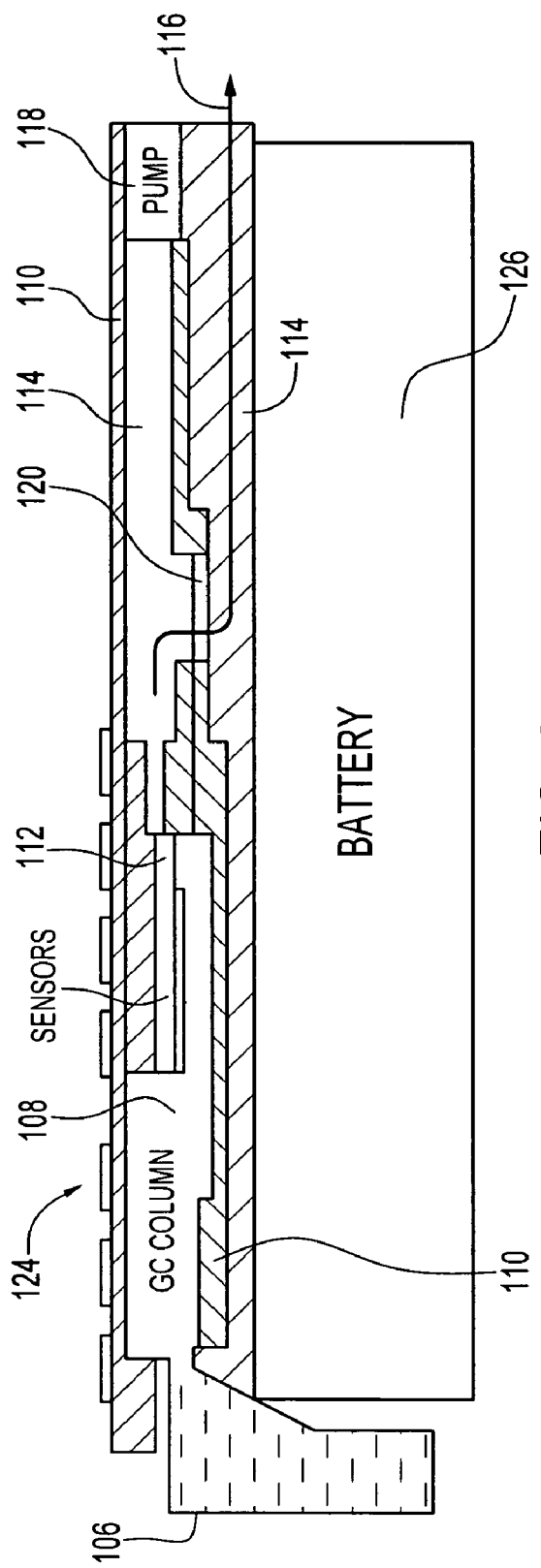
FIG. 8 is a schematic view that shows an array according to an embodiment of the invention, packaged with microelectronics and supporting structure.

FIG. 8 shows an exemplary packaging for an analysis system of the invention integrated with electronics. A collection device 106 having a plate array and narrowed end in accordance with FIG. 5 delivers analyte into a GC column 108 formed into one or more substrates 110 with GC sensors 112 and hollow portions 114 to permit fluid flow 116. Fluid flow is controlled by a pump 118 and valve 120 under the control of integrated electronics 124. The analysis system is powered by a battery 126, such as a lithium ion battery.

Figure 9:
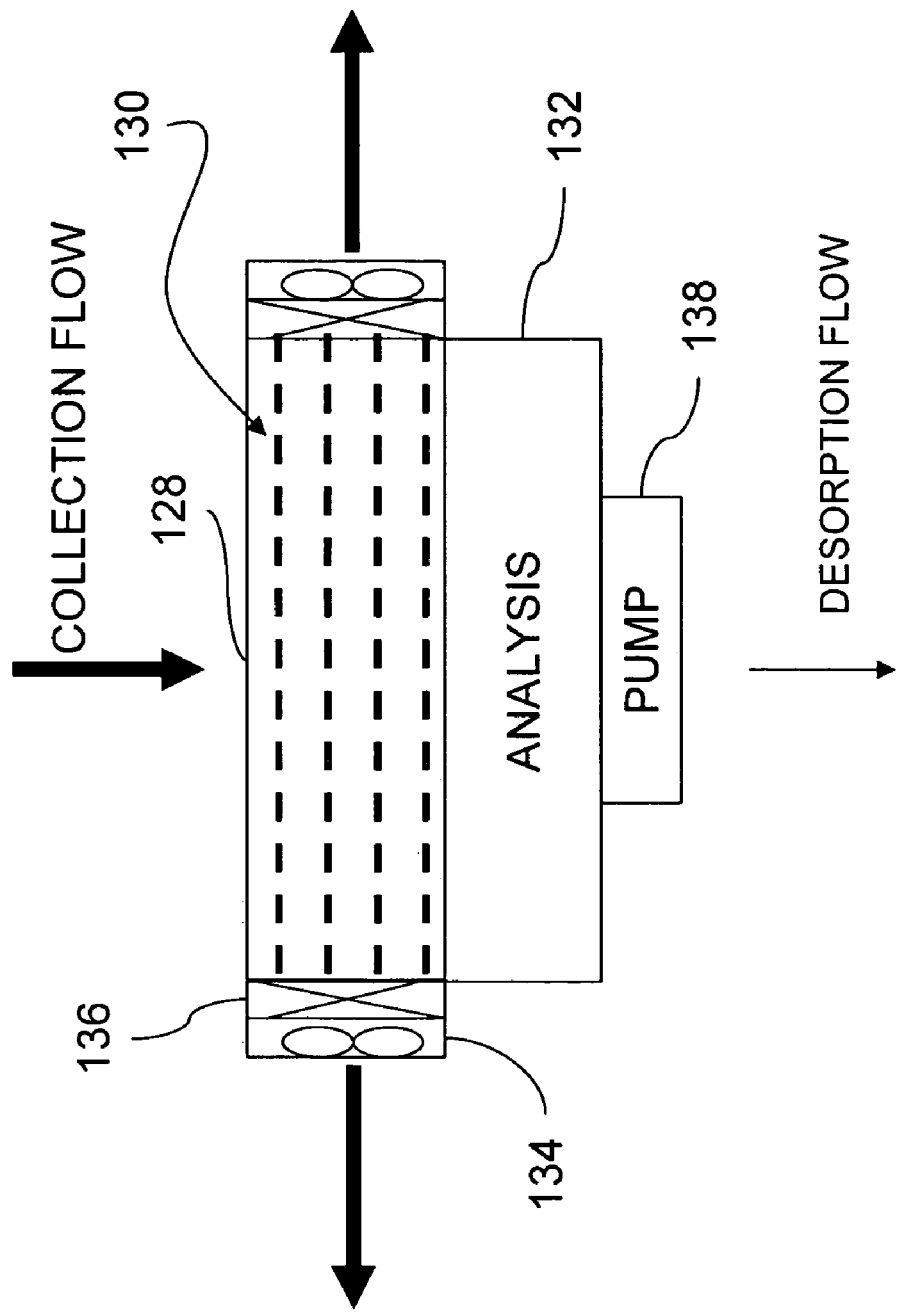
FIG. 9 is a schematic diagram of an analyte collection and analysis system in accordance with another embodiment of the invention.

FIG. 9 shows an analyte collection and analysis system in accordance with another embodiment of the invention. In FIG. 9 a high collection flow enters a housing 128 perpendicular to a flow-through micro scale plate array 130 and exits the housing 128 parallel to the plate array 130. During collection, the collection flow is blocked, such as by a valve, from entering a detection and analysis system 132. The high collection flow is directed through the plates in the plate array 130 and then along the channels between plates towards fans 134. A shutter type valve 136 allows the area occupied by the fans to be sealed to create a different fluid flow path for a low desorption flow, under the control of a micro pump 138 into the detection and analysis system 132. During thermal heating of the collector plates in the plate array 130, the fans 134 are off and the shutter valves 136 are closed. The micro pump 138 pulls a low rate desorption flow through the heated plates and directs analyte into the detection and analysis system 132.

As discussed above, using different sorbent materials, it is possible, for example, to target different agents and toxic industrial chemicals (TICS). Desorption is by heating. In the case of multiple types of sorbent, there can be a thermal desorption sequence constructed based upon desorbing temperatures. Various types of sorbent materials may be used, e.g., micro porous materials, sol-gel oxides and polymers. Example sorbent coatings include sorbent polymer(s) that act to selectively collect and concentrate analyte at ambient temperatures.

Functionalized polycarbosilanes have been used as sorbent coatings on the surface of these collector devices. Representative coatings for the sorption of hydrogen bond basic and dipolar analytes are shown in FIGS. 10A-10D, including a sorbent coating that we refer to as "NRL HC". Other functional groups are more appropriate for other types of analytes.

In addition to chemoselective polymer films, other materials may be used as sorbent coatings on the collector devices. Such materials include various forms of carbon including carbon nanotubes, nanostructured ceramic or polymer particles and films, composite materials, block copolymers, and combinations thereof.

Artisans will find guidance for selecting appropriate sorbent materials in "Choosing Polymer Coatings for Chemical Sensors," McGill, R. A.; Abraham, M. H.; Grate, J. W. CHEMTECH 24, 9 (1994) p. 27-37. Preferred sorbent coatings will have high temperature stabilities, which are necessary for thermal cycling.

The material for the plates may be any material amenable to micro fabrication processing. This includes semiconductors and dielectrics. Silicon semiconductors are suitable, as are Group III-V materials. Dielectrics include ceramics, glass, polymers, crystalline quartz, fused silica, resins, etc.

Silicon carbide is another example material, and would be suitable for high temperature applications. At relatively high air velocities, particles in the air including biomaterials, including biological agents, can be collected by impaction or other means on the surfaces of the plate(s), and after collection, this material can be released by heating to biomaterial decomposition temperatures, followed by analysis of the products of decomposition by a variety of analytical techniques. The temperatures required for decomposition may require the use of materials with properties offered by silicon carbide.

Other heating mechanisms may also be used in embodiments of the invention, including, for example, radiation induced heating or heating by conduction or convection mechanisms. However, the resistive trace is a preferred embodiment, and provides the highly desirable rapid heating to deliver a concentrated pulse. If another heating mechanism is used, it should be configured to produce the rapid desorption effect.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. An analyte collection device, the device comprising:
a first micro scale plate having a narrowed end;
sorbent coating on at least a portion of said first micro scale plate;
a penetrating hole through said first micro scale plate, said hole being arranged to permit passage of an analyte fluid flow through said first micro scale plate; and
a heating element for heating said sorbent coating;
wherein said first micro scale plate comprises a collection zone for collecting analyte from environment and a delivery zone for delivering the analyte from the device;
wherein said heating element comprises a plurality of resistive traces formed on or within said first micro scale plate;
wherein said resistive traces divide said micro scale plate into the collection zone and the delivery zone; and
wherein the delivery zone has a smaller area on said first micro scale plate than the collection zone for concentrating analyte from the collection zone in the smaller area and delivering the analyte to a detector system;
wherein the narrowed end is disposed in the delivery zone.

2. The device of claim 1, wherein said heating element comprises a resistive trace formed on or within said first micro scale plate.

3. The device of claim 1, wherein said penetrating hole comprises a plurality of penetrating holes through said first micro scale plate.

4. The device of claim 3, wherein said narrowed end is sized to match an inlet of a detector system.

5. The device of claim 4, comprising multiple sorbent coatings formed in multiple zones of said first micro scale plate, each sorbent coating being selected to sorb a predetermined analyte.

6. The device of claim 5, comprising separate heating elements for each of said multiple zones.

7. The device of claim 6, wherein said narrowed end is sized to match the inlet of one of a capillary gas chromatographic column, a narrow orifice inlet to a mass spectrometer, and a micro sensor pneumatic manifold opening.

8. The device of claim 1, wherein said sorbent coating is formed thicker in said smaller delivery zone than in said collection zone.

9. The device of claim 1, further comprising a second micro scale plate with a narrowed end, sorbent coating, a penetrating hole, and heating element, said second micro scale plate being arranged downstream of said first micro scale plate such that an analyte fluid flow substantially perpendicular to said first micro scale plate is directed through said first micro scale plate and subsequently through said second micro scale plate.

10. A self contained micro analytical system, comprising
a collection device according to claim 9;
a detector system;
a power source; and
a controller;
wherein said controller drives said heating element with a pulse width modulation (PWM) signal.

11. The device of claim 9, wherein each of said first and second micro scale plates comprises a plurality of penetrating holes.

12. The device of claim 11, wherein said penetrating holes through said first micro scale plate are at least partially aligned with solid portions of said second micro scale plate to induce a cascading flow of analyte fluid through said first and second micro scale plates.

13. The device of claim 12, further comprising a support for said first and second micro scale plates.

14. The device of claims 13, wherein said support comprises a housing.

15. The device of claim 13, wherein said support comprises a frame and suspension.

16. The device of claim 1, wherein said first micro scale plate is formed from a semiconductor material.

17. The device of claim 16, wherein said first semiconductor material comprises silicon.

18. The device of claim 1, wherein said first micro scale plate is formed from a dielectric material.

19. The device of claim 18, wherein said dielectric material comprises one of polymers, ceramics, glass, crystalline quartz, fused silica, and resins.

20. The device of claim 19, wherein said dielectric material comprises polyimide.

21. The device of claim 1, wherein said penetrating hole comprises a plurality of penetrating holes taking up approximately 40-60% of the surface area of said first micro scale plate.

22. The analyte collection device of claim 1, wherein said first micro scale plate is asymmetrical.

23. A self contained micro analytical system, comprising:
an analyte collection device, the comprising:
a first micro scale plate having a narrowed end;
sorbent coating on at least a portion of said first micro scale plate;
a penetrating hole through said first micro scale plate, said hole being arranged to permit passage of an analyte fluid flow through said first micro scale plate;
a heating element for heating said sorbent coating, wherein said first micro scale plate comprises a collection zone for collecting analyte from environment and a delivery zone for delivering the analyte from the device; and
a second micro scale plate with a narrowed end, sorbent coating, a penetrating hole, and a heating element, said second micro scale plate being arranged downstream of said first micro scale plate such that an analyte fluid flow substantially perpendicular to said first micro scale plate is directed through said first micro scale plate and subsequently through said second micro scale plate;
a detector system;
a power source; and
a controller;
wherein said controller drives said heating element with a pulse width modulation(PWM) signal;
wherein the system further comprises:
a housing for the collection device;
an inlet to said housing;
an outlet from said housing;
means for inducing flow for analyte collection; and
means for inducing flow for the analyte from the collection zone to the delivery zone;
wherein the narrowed end of said first micro scale plate and the narrowed end of said second micro scale plate are sized to match an inlet of said detector system to interface with said detector system.

24. The system of claim 23, wherein said means for inducing flow for analyte collection comprises a low power fan.

25. An analyte collection device, the device comprising:
a micro scale plate;
a penetrating hole through said micro scale plate, said hole being arranged to permit passage of an analyte fluid flow through said micro scale plate;
a first resistive trace forming a first heating element defining a first zone on said micro scale plate;
a second resistive trace forming a second heating element defining a second zone on said micro scale plate; and
sorbent coating formed on at least a portion of said first zone and a portion of said second zone;
wherein said first zone comprises a collection zone for concentrating analyte from environment and said second zone comprises a delivery zone for concentrating analyte from the collection zone in a smaller area and delivering the analyte to a detector system;
wherein said sorbent coating is thicker in said second zone than in said first zone; and
wherein said sorbent coating in said first zone and said second zone comprises the same sorbent material.

26. The device of claim 25, wherein said second zone is smaller than said first zone.

27. A self contained micro analytical system, comprising:
an analyte collection device, the device comprising:
a micro scale plate having a narrowed end;
sorbent coating on at least a portion of said micro scale plate;

a penetrating hole through said micro scale plate, said
      hole being arranged to permit passage of an analyte
      fluid flow through said micro scale plate; and
   a heating element for heating said sorbent coating,
      wherein said micro scale plate comprises a collection
      zone for collecting analyte from environment and a
      delivery zone for delivering the analyte from the
      device;
a detector system;
an airflow system;
a power source; and
a controller, wherein said controller controls said airflow
   system;
wherein the system further comprises:
a housing for the collection device;
an inlet to said housing; and
an outlet from said housing;
wherein the narrowed end of micro scale plate is sized to
   match an inlet of said detector system to interface with
   said detector system; and
wherein said controller controls said airflow system to
   induce flow through said micro scale plate for analyte
   collection and, subsequently, to induce flow from the
   collection zone to the delivery zone.

* * * * *